US006471982B1

(12) United States Patent
Lydon et al.

(10) Patent No.: US 6,471,982 B1
(45) Date of Patent: Oct. 29, 2002

(54) WOUND DRESSING

(75) Inventors: Michael James Lydon, Flintshire (GB); Douglas Queen, Buckinghamshire (GB)

(73) Assignee: Bristol-Myers Squibb Company, New York, NY (US)

( * ) Notice: Subject to any disclaimer, the term of this patent is extended or adjusted under 35 U.S.C. 154(b) by 1014 days.

(21) Appl. No.: 08/663,131

(22) PCT Filed: Jan. 20, 1995

(86) PCT No.: PCT/GB95/00114

§ 371 (c)(1),
(2), (4) Date: Jun. 17, 1996

(87) PCT Pub. No.: WO95/19795

PCT Pub. Date: Jul. 27, 1995

(30) Foreign Application Priority Data

Jan. 20, 1994 (GB) .......................................... 94 00 994

(51) Int. Cl.[7] .......................... A61F 13/00; A61L 15/00

(52) U.S. Cl. ...................................... 424/443; 424/445
(58) Field of Search ................................ 424/402, 443, 424/444, 445, 446, 449; 264/103; 128/284

(56) References Cited

U.S. PATENT DOCUMENTS

| 4,063,558 | A | * | 12/1977 | Smith .......................... 128/284 |
| 4,169,121 | A | * | 9/1979 | Pietch et al. ................. 264/103 |
| 4,775,579 | A | * | 10/1988 | Hagy et al. .................. 428/284 |
| 5,135,472 | A | * | 8/1992 | Hermann et al. ............. 602/41 |
| 5,200,195 | A | * | 4/1993 | Dong et al. .................. 424/473 |
| 5,540,922 | A | * | 7/1996 | Fabo ........................... 424/402 |

* cited by examiner

Primary Examiner—Michael G. Hartley
(74) Attorney, Agent, or Firm—John M. Kilcoyne

(57) ABSTRACT

The invention provides a wound dressing comprising in sheet form a mixture of textile fibers and gel forming fibers. The wound dressing according to the invention may have the advantages that it is non-adherent to wound tissue while being absorbent and relatively inexpensive.

13 Claims, No Drawings

WOUND DRESSING

This application is a 371 of PCT/GB95/00114, filed Jan. 20, 1995.

This invention relates a would dressing and in particular a non-adherent wound dressing comprising fibrous material.

The invention also relates to a method of treating a wound comprising applying the dressing to a wound.

It is well known that the cleansing and debriding of wounds and the removal of wound exudate is important to the process of healing wounds. Commonly used wound dressings comprise gauze, foams, sponges, cotton wads or other fibrous materials. Gauze and other fibrous materials absorb fluids by capillary action with the disadvantage that when new tissue is formed as part of the healing process, it engulfs the fibres and is torn when the material is removed causing wound injury.

There thus exists a need for a dressing which is non-adherent while being absorbent.

It is known in the art to make absorbent fibres which are capable of forming a gel on contact with water. Such fibres tend to be rather expensive and the cost of a gauze or bandage made solely from such gel forming fibres prohibitive for some wound care applications.

We have now found that it is possible to make a wound dressing comprising a mixture of textile fibres and gel forming fibres which mitigates the disadvantages mentioned above.

Accordingly the present invention provides a wound dressing comprising in sheet form a mixture of textile fibres and gel forming fibres.

The wound dressing according to the invention may have the advantages that it is non-adherent to wound tissue while being absorbent and relatively inexpensive and the added advantage that it may be retained on the wound for longer periods of time than conventional cotton gauze. This results in fewer changes of the dressing being needed which reduces material costs and health care personnel time. In addition a moist wound environment may be created which has been found to be beneficial to wound healing.

The dressing preferably comprises from 50% to 95% by weight of textile fibres and from 5% to 50% by weight of gel forming fibres. More preferably the dressing comprises from 75% to 90% by weight of textile fibres and particularly 80% by weight and from 10% to 25% of gel forming fibres and more particularly 20% by weight.

The textile fibres for use in the present invention can be natural or synthetic but are preferably cellulosic fibres for example viscose rayon, multi-limbed viscose, cotton, or regenerated cellulose or fibres having a higher absorbency than most textile fibres such as the multi-limbed cellulose fibres as described in EP-A-301874. In general textile fibres absorb liquids by capillary action and are not hygroscopic this means that their absorbancies as measured by the free swell absorbancy test are low such as less than 1 gram of liquid per gram of fibre.

The gel forming fibres for use in the present invention are hygroscopic fibres which upon the uptake of wound exudate become moist and slippery or gelatinous and thus reduce the tendancy for the surrounding fibres to adhere to the wound. The gel forming fibres can be of the type which retain their structural integrity on absorbtion of exudate or can be of the type which lose their fibrous form and become a structure-less gel or a solution on absorbtion of exudate. The gel forming fibres are preferably spun sodium carboxymethyl-cellulose fibres, chemically modified cellulosic fibres, in particular carboxymethylated cellulose fibres as described in PCT WO/9312275, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method) and a tenacity of at least 10 cN/tex. The production of solvent-spun cellulose fibres is described for example in U.S. Pat. No. 4,246,221 and U.S. Pat. No. 4,196,281 as well as in PCT WO/9312275 mentioned above. The alginate fibres are preferably of the highly absorbent type as described in WO 9417227 and WO 9400164.

Preferably the gel forming fibres for use in the present invention have an absorbency of at least 15 g/g as measured in the free swell absorbency method, more preferably between 25 g/g and 50 g/g. The degree of substitution of the cellulosic gel forming fibre is preferably at least 0.2 carboxymethyl groups per glucose unit, more preferably between 0.3 and 0.5. The tenacity of the fibre is preferably in the range 25–15 cN/tex.

The gel forming fibres suitable for use in the present invention can be processed using conventional textile machinery, for example by the staple route including cutting, carding and if desired crimping, drafting and spinning.

The wound dressing of the present invention is in sheet form and may be made by intimately mixing the gel forming fibres with the textile fibres, for example by carding or air-laying the fibres together to form a web of mixed fibres. Alternatively the wound dressing of the present invention may be made by spinning or twisting the gel forming fibres and the textile fibres together to form a yarn and then knitting or weaving the yarn to form a bandage or stocking. The wound dressing of the present invention may be in the form of swabs, wound pads, wadding ribbons, sponges, nets and bandages and may be used as a primary or secondary dressing especially in the treatment of leg ulcers.

Various optional ingredients can also be included in the final composition such as preservatives and small amounts of pharmacologically active ingredients. For example an antibiotic or antimicrobial agent such as metronidazole, silver sulphadiazine, neomycin or penicillin and antiseptic agent such as povidone iodine and antiinflammatory agent such as hydrocortisone or triamcinolone acteonide or a skin protective agent such as a zinc oxide can be included. The invention is illustrated by the following examples:

EXAMPLE 1

Gel forming fibres were made as follows:

A tow of 1.7 decitex solvent-spun cellulosic fibres, the fibres having a substantially uniform structure across their cross-section, as sold under the Trade Mark "Tencel" was obtained in a never-dried state. The tow was passed through a hand mangle. The amount of water left on the tow after mangling was 62%. This wet tow was placed in a solution containing 7.5% sodium hydroxide and 22.1% sodium monochloroacetate at room temperature for 2 minutes. The padded tow was mangled again and reacted in a conditioning cabinet set at 23% RH and 90° C. for five minutes.

After that treatment the tow was washed in a solution containing 55% industrial alcohol, 42% water and 3% acetic acid. The washed tow was then treated with a finish containing 99% industrial alcohol and 1% Atlas 61086 emulsifier. The tow was dried at low temperature, leaving some residual moisture on the fibres. The finished tow was cut into fibres.

The fibres had a degree of substitution above 0.1, a tenacity of 22.5 cN/tex and an extensibility of 12%. The free swell absorbency of the fibres was measured by the free swell absobancy method by dispersing 0.5 g fibre in 30 ml of 0.9% saline solution and leaving for 5 minutes. The dispersion was then filtered through a sintered Mark 1 funnel of pore size 100–160 microns and was left for 5 minutes, or until it stopped dripping. The water filtered through the funnel was weighed and the weight of water absorbed by the fibres calculated by subtraction. The absorbency was 30 g/g.

20% by weight of gel-forming fibres produced according to the above method were carded in a blend with 80% multi-limbed regenerated cellulose fibres (Galaxy) to form a web of size 10 cm×10 cm. The carded web was then sealed in a foil envelope and sterilized t o form a wound dressing.

The wound dressing when in contact with a wound will absorb exudate causing the gel forming fibres to swell and form a gel. The gel will render the wound dressing sufficiently slippery to prevent adherence of the dressing to the newly forming tissue.

EXAMPLES 2–5

Gel forming fibres were produced as follows:

A tow of never-dried Tencel fibres of filament decitex 1.7 was padded with a solution of sodium hydroxide and sodium monochloroacetate. The concentrations of the reagents differed as shown in the table below. The tow was lightly mangled to stop dripping and dried at 90° C. to a moisture level of 13%.

The resulting tow was washed in a solution containing 55% ethanol, 42% water, 2.5% acetic acid and 0.5% citric acid.

The washed tow was treated with a finish and dried as ed in Example 1.

| Example No. | Concentrations of Reagents % | | Degree of substitution | Free Swell Absorbency g/g |
|---|---|---|---|---|
| | Na OH | ClCH2 COONa | | |
| 2 | 4.5 | 13.3 | 0.235 | 20 |
| 3 | 5.5 | 16.2 | 0.29 | 18 |
| 4 | 6.5 | 19.2 | 0.375 | 28 |
| 5 | 7.5 | 22.1 | 0.405 | 38 |

The tow of filaments produced in each example above was cut into 50 mm lengths and 50% by weight of the gel-forming fibres was carded in a blend with 50% viscose rayon fibre (Galaxy) to form a non-woven fabric. The fabric was then sealed in a foil envelope and sterilized to form a wound dressing.

What is claimed is:

1. A non-adherent wound dressing in sheet form comprising from 50% by weight to 95% by weight of textile fibres mixed with from 5% by weight to 50% by weight of gel forming fibres.

2. A wound dressing as claimed in claim 1 comprising from 75% to 90% by weight of textile fibres and 10% to 25% by weight of gel forming fibres.

3. A wound dressing as claimed in claim 1 wherein the textile fibres are cellulosic fibres.

4. A wound dressing as claimed in claim 1 wherein the gel forming fibres are chemically modified cellulosic fibres.

5. A wound dressing as claimed in claim 1 wherein the gel forming fibres are alginate fibres.

6. A wound dressing as claimed in claim 1 wherein the gel forming fibres have an absorbency of at least 2 g/g.

7. A wound dressing as claimed in claim 4 wherein the fibres have a degree of substitution of at least 0.05 carboxymethyl groups per glucose unit.

8. A wound dressing as claimed in claim 1 wherein the fibres are in the form of a carded web.

9. A wound dressing as claimed in claim 1 wherein the fibres are in the form of a woven fabric.

10. A wound dressing as claimed in claim 1 wherein the fibres are in the form of a knitted stocking.

11. A method for the treatment of a wound comprising placing the dressing of claim 1 in direct contact with the wound.

12. A method for the treatment of wounds comprising mixing from about 50% by weight to about 95% by weight of textile fibers and about 5% by weight to about 50% by weight of gel forming fibers and placing the resulting mixture in direct contact with the wound.

13. A method as claimed in claim 12 wherein the wound is a chronic wound.

* * * * *